(12) United States Patent
Ouyang et al.

(10) Patent No.: US 8,304,570 B2
(45) Date of Patent: Nov. 6, 2012

(54) PREPOLYMER FOR BIOMEDICAL MATERIALS

(76) Inventors: Yun Liang Ouyang, Hsinchu County (TW); Chih Hung Chang, Taipei (TW)

( * ) Notice: Subject to any disclaimer, the term of this patent is extended or adjusted under 35 U.S.C. 154(b) by 272 days.

(21) Appl. No.: 12/704,731

(22) Filed: Feb. 12, 2010

(65) Prior Publication Data
US 2010/0286428 A1    Nov. 11, 2010

(30) Foreign Application Priority Data
May 8, 2009  (TW) ................. 98115239 A

(51) Int. Cl.
*C07F 7/10*   (2006.01)
(52) U.S. Cl. ..................................... 556/420
(58) Field of Classification Search ........................ None
See application file for complete search history.

(56) References Cited

U.S. PATENT DOCUMENTS

| | | | |
|---|---|---|---|
| 4,136,250 A | 1/1979 | Mueller et al. | |
| 4,605,712 A | 8/1986 | Mueller et al. | |
| 6,524,564 B1 | 2/2003 | Kim et al. | |
| 6,809,169 B2 | 10/2004 | Byrd et al. | |
| 2003/0232201 A1 | 12/2003 | Byrd et al. | |
| 2008/0312397 A1 | 12/2008 | Lai et al. | |

FOREIGN PATENT DOCUMENTS

| | | |
|---|---|---|
| EP | 0822952 B1 | 7/2003 |
| JP | 5-19214 A | 1/1993 |
| JP | 2002-327063 A | 11/2002 |

OTHER PUBLICATIONS

Korea Office Action dated Nov. 15, 2011 for 10-2010-0041993.
Search report issued Aug. 2, 2012 from corresponding European counterpart application No. 10156845.9 cites US 4605712 A, 2003/232201 A1, and EP 0822952 B1.
Office action dated Aug. 31, 2012 from TW counterpart application No. 098115239 cites JP 2002-327063A, JP 5-19214A and US 6524564B1.
English abstract of Office action dated Aug. 31, 2012 from TW counterpart application No. 098115239.
English abstract of JP 2002-327063A and JP 5-19214A.

*Primary Examiner* — Yevegeny Valenrod
(74) *Attorney, Agent, or Firm* — WPAT, P.C.; Anthony King

(57) ABSTRACT

A prepolymer for biomedical materials has the following formula:

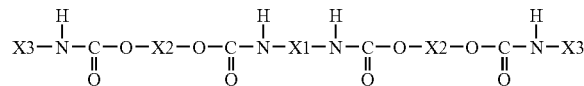

wherein X1 represents aliphatic compounds or aromatic compounds, X3 represents alkene-containing compounds, and X2 represents siloxane compounds having the following formula.

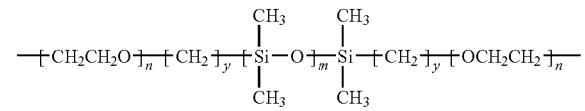

In one embodiment of the present invention, n is between 1 and 20, m is between 10 and 20, and y is between 1 and 7.

2 Claims, No Drawings

PREPOLYMER FOR BIOMEDICAL MATERIALS

BACKGROUND OF THE INVENTION (A) Field of the Invention

The present invention relates to a prepolymer for biomedical materials, and more particularly, to a prepolymer for biomedical materials with gas permeability, oxygen permeability and wettability.

(B) Description of the Related Art

A material's suitability for biomedical application depends on factors such as the wettability, oxygen permeability, adhesion and reactivity with the biomedical material such as protein and lipid. Generally, the medical employee currently uses gauze as the dressing for lacerations to prevent the laceration from being infected. However, gauze can not prevent water from evaporating through the surface of the laceration. Furthermore, replacing the gauze dressing is likely to destroy the healing of the cut.

Recently, researchers have developed the laceration dressing made of the polymer material such as the siloxane-containing polymer, which can eliminate the disadvantages of the conventional gauze. In addition, high oxygen permeability, better wettability and anti-adhesion characteristic are important concerns in the opthamology application such as contact lens and Ophthalmic implants material.

SUMMARY OF THE INVENTION

One aspect of the present invention provides a prepolymer for biomedical materials, which provides adjustable gas permeability, oxygen permeability, hydrophilic and wettability characteristic by changing the number of the ligands.

A prepolymer for biomedical materials according to this aspect of the present invention comprises compounds having the following formula:

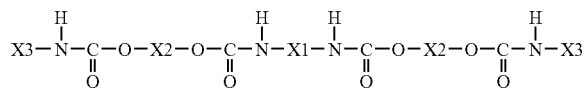

wherein X1 represents aliphatic compounds or aromatic compounds, X3 represents alkene-containing compounds serving as reaction terminals for preparing the biomedical materials, and X2 represents siloxane compounds having the following formula:

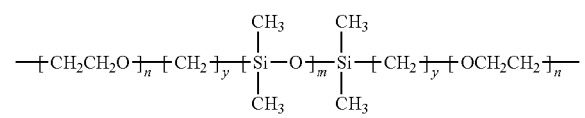

In one embodiment of the present invention, n is between 1 and 20, m is between 10 and 20, and y is between 1 and 7.

The foregoing has outlined rather broadly the features and technical advantages of the present invention in order that the detailed description of the invention that follows may be better understood. Additional features and advantages of the invention will be described hereinafter, which form the subject of the claims of the invention. It should be appreciated by those skilled in the art that the conception and specific embodiment disclosed may be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

DETAILED DESCRIPTION OF THE INVENTION

In one embodiment of the present disclosure, the prepolymer for biomedical materials comprises compounds having the following formula:

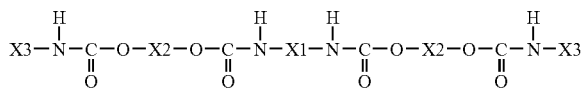

wherein X1 represents aliphatic compounds or aromatic compounds, X3 represents alkene-containing compounds serving as reaction terminals for preparing the biomedical materials, and X2 represents siloxane compounds having the following formula:

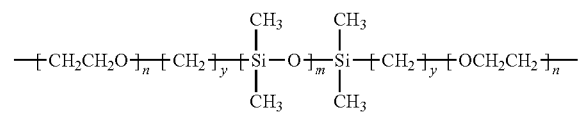

For example, the aliphatic compounds can be butane, octane, or hexane, and the aromatic compounds can be phenylene. The gas permeability and oxygen permeability of the prepolymer can be adjusted by changing the m value of the X2, and the hydrophilic ability or wettability can be adjusted by changing the n value of the X2 such that the prepolymer can be applied to the material requiring high oxygen permeability and high wettability such as medical dressing and contact lenses. In one embodiment of the present invention, n is between 1 and 20, and m is between 10 and 20.

In addition, the carbon number between the silicon atom and the ether ligand (the y value) can be adjusted to provide desired properties, including increasing the carbon number to improve the ductility and decreasing the carbon number to improve the strength. In one embodiment of the present invention, y is between 1 and 7.

The following describes a method for preparing the prepolymer:

Compounds are used which have diisocyanate ligand to react with compounds having siloxane and two hydroxy ligands such that the isocyanate ligand reacts with the hydroxy ligand. The compounds having diisocyanate ligand can be 1,3-Phenylene diisocyanate, 1,4-Diisocyanatobutane, 1,6-Diisocyanatohexane, 1,4-Phenylene diisocyanate, 1,8-Diisocyanatooctane, or Toluene 2,4-diisocyanate. The compounds having siloxane and two hydroxy ligands may have the following formula:

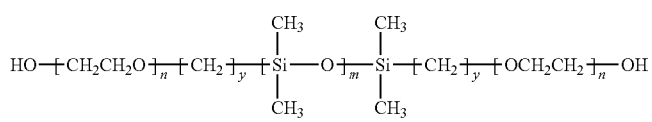

Subsequently, alkene-containing compounds are added which have isocyanate ligand and acrylate ligand (or methacrylate ligand) to react so as to form the prepolymer for biomedical materials. In particular, the prepared prepolymer includes alkene-containing ligand serving as reaction terminals for preparing the biomedical materials.

In another embodiment of the present disclosure, the prepolymer for biomedical materials comprises compounds having the following formula:

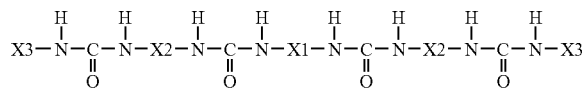

wherein X1 represents aliphatic compounds or aromatic compounds, X3 represents alkene-containing compounds serving as reaction terminals for preparing the biomedical materials, and X2 represents siloxane compounds having the following formula:

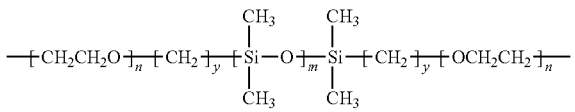

For example, the aliphatic compounds can be butane, octane, or hexane, and the aromatic compounds can be phenylene. The gas permeability and oxygen permeability of the prepolymer can be adjusted by changing the m value of the X2, and the hydrophilic characteristic or wettability can be adjusted by changing the n value of the X2 such that the prepolymer can be applied to the material requiring high oxygen permeability and high wettability such as medical dressing and contact lenses. In one embodiment of the present invention, n is between 1 and 20, and m is between 10 and 20.

In addition, the carbon number between the silicon atom and the ether ligand (the y value) can be adjusted to provide desired properties, including increasing the carbon number to improve the ductility or decreasing the carbon number to improve the strength. In one embodiment of the present invention, y is between 1 and 7.

The following describes another method for preparing the prepolymer:

Compounds are used which have diisocyanate ligand to react with compounds having siloxane and two amine ligands such that the isocyanate ligand reacts with the amine ligand. The compounds having diisocyanate ligand can be 1,3-Phenylene diisocyanate, 1,4-Diisocyanatobutane, 1,6-Diisocyanatohexane, 1,4-Phenylene diisocyanate, 1,8-Diisocyanatooctane, or Toluene 2,4-diisocyanate. The compounds having siloxane and two amine ligands may have the following formula:

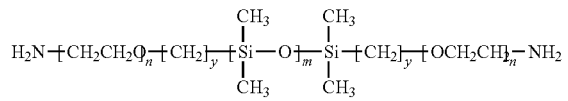

Subsequently, alkene-containing compounds are added which have isocyanate ligand and acrylate ligand (or methacrylate ligand) to react so as to form the prepolymer for biomedical materials. In particular, the prepared prepolymer includes alkene-containing ligand serving as reaction terminals for preparing the biomedical materials.

In another embodiment of the present disclosure, the prepolymer for biomedical materials comprises compounds having the following formula:

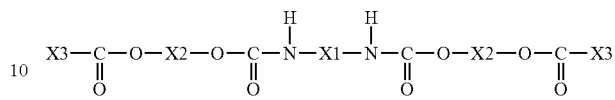

wherein X1 represents aliphatic compounds or aromatic compounds, X3 represents alkene-containing compounds serving as reaction terminals for preparing the biomedical materials, and X2 represents siloxane compounds having the following formula.

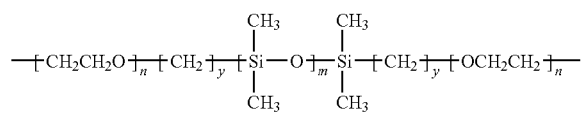

For example, the aliphatic compounds can be butane, octane, or hexane, and the aromatic compounds can be phenylene. The gas permeability and oxygen permeability of the prepolymer can be adjusted by changing the m value of the X2, and the hydrophilic characteristic or wettability can be adjusted by changing the n value of the X2 such that the prepolymer can be applied to the material requiring high oxygen permeability and high wettability, such as medical dressing and contact lenses. In one embodiment of the present invention, n is between 1 and 20, and m is between 10 and 20.

In addition, the carbon number between the silicon atom and the ether ligand (the y value) can be adjusted to provide desired properties, including increasing the carbon number to improve the ductility or decreasing the carbon number to improve the strength. In one embodiment of the present invention, y is between 1 and 7.

The following describes another method for preparing the prepolymer:

Compounds are used which have diisocyanate ligand to react with compounds having siloxane and two hydroxy ligands such that the isocyanate ligand reacts with the hydroxy ligand. The compounds having diisocyanate ligand can be 1,3-Phenylene diisocyanate, 1,4-Diisocyanatobutane, 1,6-Diisocyanatohexane, 1,4-Phenylene diisocyanate, 1,8-Diisocyanatooctane, or Toluene 2,4-diisocyanate. The compounds having siloxane and two hydroxy ligands may have the following formula:

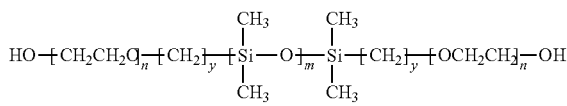

Subsequently, alkene-containing compounds are added which have chlorine ligand and acrylate ligand (or methacrylate ligand) such as methacryloyl chloride, acryloyl chloride to react so as to form the prepolymer for biomedical materials. In particular, the prepared prepolymer includes alkene-containing ligand serving as reaction terminals for preparing the biomedical materials.

In another embodiment of the present disclosure, the prepolymer for biomedical materials comprises compounds having the following formula:

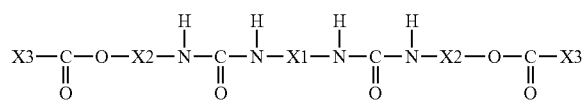

wherein X1 represents aliphatic compounds or aromatic compounds, X3 represents alkene-containing compounds serving as reaction terminals for preparing the biomedical materials, and X2 represents siloxane compounds having the following formula:

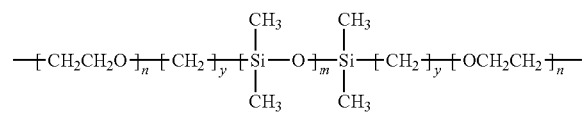

For example, the aliphatic compounds can be butane, octane, or hexane, and the aromatic compounds can be phenylene. The gas permeability and oxygen permeability of the prepolymer can be adjusted by changing the m value of the X2, and the hydrophilic characteristic or wettability can be adjusted by changing the n value of the X2 such that the prepolymer can be applied to the material requiring high oxygen permeability and high wettability, such as medical dressing and contact lenses. In one embodiment of the present invention, n is between 1 and 20, and m is between 10 and 20.

In addition, the carbon number between the silicon atom and the ether ligand (the y value) can be adjusted to provide desired properties, including increasing the carbon number to improve the ductility or decreasing the carbon number to improve the strength. In one embodiment of the present invention, y is between 1 and 7.

The following describes another method for preparing the prepolymer:

Compounds are used which have diisocyanate ligand to react with compounds having siloxane and two amine ligands such that the isocyanate ligand reacts with the amine ligand. The compounds having diisocyanate ligand can be 1,3-Phenylene diisocyanate, 1,4-Diisocyanatobutane, 1,6-Diisocyanatohexane, 1,4-Phenylene diisocyanate, 1,8-Diisocyanatooctane, or Toluene 2,4-diisocyanate. The compounds having siloxane and two amine ligands may have the following formula:

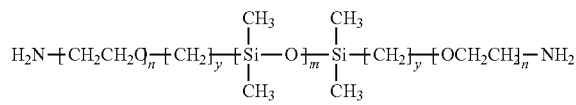

Alkene-containing compounds are added which have chlorine ligand and acrylate ligand (or methacrylate ligand) such as methacryloyl chloride or acryloyl chloride to react so as to form the prepolymer for biomedical materials. In particular, the prepared prepolymer includes alkene-containing ligand serving as reaction terminals for preparing the biomedical materials.

Although the present invention and its advantages have been described in detail, it should be understood that various changes, substitutions and alterations can be made herein without departing from the spirit and scope of the invention as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A prepolymer for biomedical materials, comprising compound having the following chemical formula:

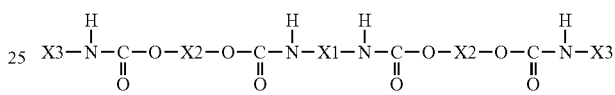

wherein X1 represents an aliphatic compound or an aromatic compound, X2 represents a siloxane compound, and X3 represents an alkene-containing compound;
wherein X2 has the following chemical formula:

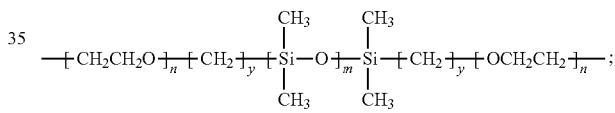

wherein n is an integer between 1 and 20;
wherein m is an integer between 10 and 20;
wherein y is an integer between 1 and 7.

2. A prepolymer for biomedical materials, comprising compound having the following chemical formula:

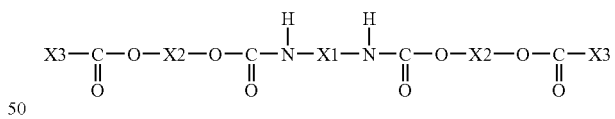

wherein X1 represents an aliphatic compound or an aromatic compound, X2 represents a siloxane compound, and X3 represents an alkene-containing compound;
wherein X2 has the following chemical formula:

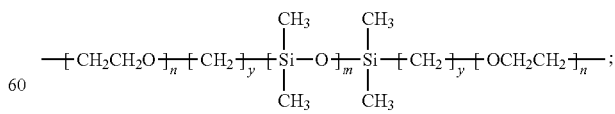

wherein n is an integer between 1 and 20;
wherein m is an integer between 10 and 20;
wherein y is an integer between 1 and 7.

* * * * *